United States Patent
Glos

(10) Patent No.: US 7,767,769 B2
(45) Date of Patent: Aug. 3, 2010

(54) METHOD FOR THE ESTERIFICATION OF ALCOHOLS WITH OLEFINICALLY UNSATURATED CARBOXYLIC ACIDS

(75) Inventor: Martin Glos, Essen (DE)

(73) Assignee: Clariant Produkte (Deutschland) GmbH, Frankfurt (DE)

( * ) Notice: Subject to any disclaimer, the term of this patent is extended or adjusted under 35 U.S.C. 154(b) by 1052 days.

(21) Appl. No.: 10/580,384

(22) PCT Filed: Nov. 11, 2004

(86) PCT No.: PCT/EP2004/012790

§ 371 (c)(1),
(2), (4) Date: May 22, 2006

(87) PCT Pub. No.: WO2005/049544

PCT Pub. Date: Jun. 2, 2005

(65) Prior Publication Data

US 2007/0149803 A1    Jun. 28, 2007

(30) Foreign Application Priority Data

Nov. 22, 2003   (DE) ................... 103 54 652

(51) Int. Cl.
C07C 67/14   (2006.01)
C07C 67/08   (2006.01)
C07C 67/02   (2006.01)
C07C 69/54   (2006.01)

(52) U.S. Cl. ..................................... 526/74
(58) Field of Classification Search ............. None
See application file for complete search history.

(56) References Cited

U.S. PATENT DOCUMENTS

| | | | |
|---|---|---|---|
| 5,872,252 A | 2/1999 | Sutoris | |
| 6,040,473 A * | 3/2000 | Knebel et al. | 560/217 |
| 6,297,314 B1 * | 10/2001 | Hintze-Bruning et al. | 524/589 |
| 6,818,791 B2 | 11/2004 | Martin | |
| 6,872,848 B2 | 3/2005 | Kroner | |
| 2001/0023302 A1 | 9/2001 | Iwakura | |
| 2002/0193624 A1 | 12/2002 | Zirnstein | |
| 2004/0168903 A1 | 9/2004 | Geisendorfer | |

FOREIGN PATENT DOCUMENTS

DE   100 36 879   9/2001
JP   2003-313153   11/2003

OTHER PUBLICATIONS

English language abstract of DE 100 36 879, Sep. 20, 2001.
English Language Machine Translation of JP 2003-313153, Nov. 6, 2003.
PCT Search Report PCT/EP2004/012790, mailed Apr. 28, 2005.
Translation of PCT International Preliminary Report on Patentability PCT/EP2004/012790, mailed Oct. 2006.

* cited by examiner

*Primary Examiner*—Daniel M Sullivan
*Assistant Examiner*—Yevegeny Valenrod
(74) *Attorney, Agent, or Firm*—Tod A. Waldrop

(57) ABSTRACT

The invention relates to a method for producing esters from alcohols and olefinically unsaturated carboxylic acids by reacting an alcohol with an olefinically unsaturated carboxylic acid or a reactive derivative thereof, in the presence of between 1 ppm and 1 wt. % of at least one oxazoline of formula 1,

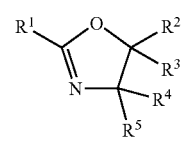

(1)

in relation to the weight of the reaction mixture of alcohol and olefinically unsaturated carboxylic acid/carboxylic acid derivative, $R^1$, $R^2$, $R^3$, $R^4$ and $R^5$ representing hydrogen or branched, linear, cyclical, saturated or unsaturated hydrocarbon radicals containing up to 25 C atoms that can be substituted by heteroatoms, and $R^1$, $R^2$, $R^3$, $R^4$ and $R^5$ being the same or different.

6 Claims, No Drawings

METHOD FOR THE ESTERIFICATION OF ALCOHOLS WITH OLEFINICALLY UNSATURATED CARBOXYLIC ACIDS

The present invention relates to a method for the preparation of esters with olefinically unsaturated carboxylic acids, in which oxazolines (4,5-dihydro-1,3-oxazoles) are used as stabilizers.

Among the esters of the olefinically unsaturated carboxylic acids, the (meth)acrylates are of particular industrial interest since they are starting compounds for the preparation of polymers and copolymers which are used in various areas. The term (meth)acrylates represents methacrylates and acrylates. The present invention can therefore particularly advantageously be used for the preparation of these esters and is described below for (meth)acrylates by way of example.

In the preparation of the esters of alcohols with olefinically unsaturated carboxylic acids, various problems should be borne in mind. Firstly, olefinically unsaturated carboxylic acids tend to undergo polymerization under the influence of heat or light. Particularly in the preparation and distillative purification, they are subjected to temperatures which can easily initiate an undesired polymerization. The polymer formation may also be caused by the vapors of the unstabilized unsaturated carboxylic acid condensing on the colder reactor lid or other components of the plant and polymerizing there. The result is soiling of the apparatuses, blockage of pipes and pumps and coating of column trays and heat exchanger surfaces ("fouling"). The cleaning of the plant is a complicated, expensive and environmentally polluting process which also greatly reduces the availability of the plants.

The prior art discloses various methods for minimizing the cleaning effort.

DE 100 36 879 A1 describes a method for the preparation of esters of (meth)acrylic acid by transesterification, in which the deposition of polymer in the columns is prevented by recycling the organic phase of the distillate from that region of the column which does not have separation activity into the reaction zone.

DE 101 27 938 A1 describes a method for the preparation of (meth)acrylates by transesterification, an inert gas or gas mixture being passed through the reaction zone. In addition, a stabilizer solution is sprayed into the columns. This prevents the formation of polymer on the heat exchanger surfaces.

DE 100 63 175 A1 describes the direct esterification of higher alcohols. The basis of the method is that a reactor having a circulation evaporator is employed and a part of the distillate (cyclohexane as entraining agent) is recycled to the circulation evaporator. As a result, copper salts as stabilizers can be dispensed with.

DE 100 63 176 A1 describes a method for the preparation of higher (meth)acrylates by direct esterification of higher alcohols. Cyclohexane is used as an entraining agent. The basis of the method is that a part of the packing in the distillation column comprises copper or a copper-containing material. As a result, copper salts as stabilizers can be dispensed with.

DE 100 63 511 A1 describes a method for the preparation of alkylpolyalkylene glycol esters of monoethylenically unsaturated carboxylic acids by direct esterification. Esterification is effected at atmospheric pressure or superatmospheric pressure and the water is then distilled off only briefly at reduced pressure and the esterification is then continued at atmospheric pressure or superatmospheric pressure.

EP 874 870 A1 describes a method for the preparation of polyglycol (meth)acrylates by transesterification. Catalysts used are $Ca(OH)_2$ or mixtures with LiCl. Stabilizers used are hydroquinones or phenols or sterically hindered amines.

It was an object of the present invention to provide improved stabilizers for olefinically unsaturated carboxylic acids.

It has now surprisingly been found that esters of olefinically unsaturated carboxylic acids can be prepared using oxazolines. Use of oxazolines prevents the apparatuses used, such as, for example, pipes, columns and heat exchanges, from becoming blocked or soiled by deposits of polymers. As a result, the effort for cleaning the plants decreases and the availability of the plant is improved.

The invention therefore relates to a method for the preparation of esters from alcohols and olefinically unsaturated carboxylic acids by reacting an alcohol with an olefinically unsaturated carboxylic acid or a reactive derivative thereof, from 1 ppm to 1% by weight, based on the weight of the reaction mixture comprising alcohol and olefinically unsaturated carboxylic acid/carboxylic acid derivative, of at least one oxazoline of the formula 1

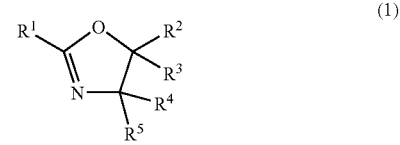

(1)

in which $R^1$, $R^2$, $R^3$, $R^4$ and $R^5$ are hydrogen or branched, straight-chain, cyclic, saturated or unsaturated hydrocarbon radicals having up to 25 carbon atoms which may be substituted by heteroatoms, and $R^1$, $R^2$, $R^3$, $R^4$ and $R^5$ may be identical or different, being present.

The invention furthermore relates to the use of compounds of the formula 1 as stabilizers in the reaction between alcohols and olefinically unsaturated carboxylic acids or the reactive derivatives thereof, from 1 ppm to 1% by weight, based on the weight of the reaction mixture comprising alcohol and carboxylic acid/carboxylic acid derivative, of the compound of the formula 1 being used.

The invention furthermore relates to a composition comprising

A) an alcohol

B) an olefinically unsaturated carboxylic acid or a reactive derivative thereof, the molar ratio A):B) being from 1:0.2 to 1:15, and C) from 1 ppm at 1% by weight, based on the total weight of A) and B), of a compound of the formula 1

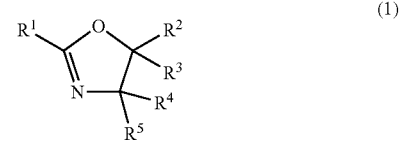

(1)

in which $R^1$, $R^2$, $R^3$, $R^4$ and $R^5$ are hydrogen or branched, straight-chain, cyclic, saturated or unsaturated hydrocarbon radicals having up to 25 carbon atoms which may be substituted by heteroatoms, and $R^1$, $R^2$, $R^3$, $R^4$ and $R^5$ may be identical or different.

In a preferred embodiment, $R^1$, $R^2$, $R^3$, $R^4$ and $R^5$, independently of one another, are hydrocarbon radicals having 1 to 12 carbon atoms, in particular hydrogen or methyl groups.

In a particularly preferred embodiment of the invention, $R^1$ is methyl $R^2$ and $R^3$ are hydrogen $R^4$ and $R^5$ are hydrogen or methyl.

The oxazolines according to the invention are used in amounts of preferably from 10 ppm to 0.5% by weight, in particular from 50 ppm to 0.1% by weight, based on the reaction mixture comprising alcohol and carboxylic acid/carboxylic acid derivative.

For the preparation of the esters according to the invention, it is possible to use various methods, such as, for example, the reaction of reactive carboxylic acid derivatives, such as, for example, acid halides or esters, with the alcohols, or the direct esterification of the olefinically unsaturated carboxylic acid with alcohols. It is possible to work both with and without a solvent.

The method according to the invention is suitable in general for the preparation of esters of unsaturated carboxylic acids, preferably alpha, beta-unsaturated carboxylic acid esters and particularly preferably for esters of olefinically unsaturated monocarboxylic acids having 3 to 6 carbon atoms and olefinically unsaturated dicarboxylic acids having 4 to 8 carbon atoms.

Preferred monoethylenically unsaturated mono- and dicarboxylic acids are acrylic acid, methacrylic acid, styrenesulfonic acid, maleic acid, fumaric acid, crotonic acid, itaconic acid and senecioic acid. It is also possible to use the corresponding anhydrides, such as, for example, maleic anhydride, or the corresponding acid chlorides. The corresponding acid esters, such as, for example, the methyl or ethyl esters, are used as starting material in the transesterification.

Alcohols which may be used are monohydric or polyhydric alcohols which may be branched, straight-chain or cyclic, saturated or unsaturated, with up to 500 carbon atoms. Such alcohols are, for example, $C_1$ to $C_{30}$-monoalcohols, such as, for example, 2-ethylhexyl, 2-propylheptyl, lauryl, stearyl or behenyl alcohol;

$C_1$ to $C_{12}$-alkyl-substituted cyclopentanols or cyclohexanols, such as, for example, tert-butylcyclohexanol;

$C_2$ to $C_{20}$-diols, such as, for example, ethylene glycol, phenylethylene glycol, 1,2- and 1,3-propylene glycol, 1,2-, 1,3- or 1,4-butylene glycol, 1,6-hexanediol and the mono-$C_1$- to $C_{30}$-alkyl ethers thereof;

aromatic monohydric or polyhydric alcohols such as, for example, phenols, resorcinol or tannin;

polyethylene and polypropylene glycols, such as, for example, diethylene glycol, triethylene glycol, tetraethylene glycol, dipropylene glycol, tripropylene glycol and the mono-$C_1$- to $C_{30}$-alkyl ethers thereof;

triols and higher polyols, such as, for example, glycerol, polyglycerols, trimethylolpropane, pentaerythritol or $C_1$- to $C_{30}$-alkyl ethers thereof with at least one free hydroxyl group;

the alkoxylated derivatives of said alcohols, such as, for example, ethoxylates, propoxylates or butoxylates.

For the preparation of the alkoxylated alcohols or phenols, one mole of an alcohol or phenol is reacted with from 1 to 300 mol of an alkylene oxide having 2 to 20 carbon atoms. Suitable alkylene oxides are, for example, ethylene oxide, propylene oxide, butylene oxide or styrene oxide. Both one alkylene oxide or a plurality of alkylene oxides and the alcohol or the phenol may be subjected to an addition reaction. If a plurality of alkylene oxides are subjected to an addition reaction, the individual alkylene oxides may be randomly distributed in the product or arranged in blocks.

Examples of alkoxylated alcohols are methylpolyethylene glycols which comprise 3, 10, 25, 40, 100 or 200 mol of ethylene oxide and are obtained by reacting methanol with 3, 10, 25, 40, 100 or 200 mol of ethylene oxide. Accordingly, long-chain alcohols, such as, for example, butanol, dodecyl alcohol, isododecyl alcohol, stearyl alcohol, behenyl alcohol, oleyl alcohol, $C_8$- to $C_{20}$-oxo alcohols, $C_3$ to $C_{20}$-alkyl phenols or aryl phenols can also be reacted with appropriate amounts of ethylene oxide.

Alcohols which comprise further heteroatoms may also be used, such as, for example, alkoxylates of primary or secondary amines, such as, for example, oleylamine ethoxylates, didecylamine ethoxylates or coconut fatty amine propoxylates, and amide alkoxylates, such as, for example, oleamide ethoxylates.

Compounds such as ethanolamine, diethanolamine, triethanolamine, 2-dimethylethan-1-ol, 3-dimethylaminopropan-1-ol, 1-dimethylaminopropan-2-ol, 2-dimethylaminopropan-1-ol, 6-dimethylaminohexan-1-ol, 2-diethylaminoethyn-1-ol, 3-diethylaminopropan-1-ol, 6-diethylaminohexan-1-ol, 2-dibutylaminoethan-1-ol, 3-dibutylaminopropan-1-ol, and 6-dibutylaminohexan-1-ol could also be used as alcohols in the context of the present invention.

The molar ratio of alcohol to unsaturated carboxylic acid is preferably in the range of from 1:0.2 to 15, in particular in the range of from 1:0.8 to 15.

In addition to the stabilizer according to the invention of the formula 1, the stabilizers known according to the prior art can be used. Conventional stabilizers are N-oxyls, such as, for example, 4-hydroxy-2,2,6,6-tetramethyl-1-oxylpiperidine, 4-oxo-2,2,6,6-tetramethylpiperidin-N-oxyl, phenols and naphthols, such as, for example, hydroquinone, naphthoquinone, p-aminophenol, p-nitrosophenol, 2-tert-butylphenol, 4-tert-butylphenol, 2,4-di-tert-butylphenol, 2-methyl-4-tert-butylphenol, 4-methyl-2,3-di-tert-butylphenol, Ionol K 65®, p-methoxyphenol or butyhydroxyanisole, or 4-amines, such as, for example, N,N-diphenylamine, phenylenediamines, such as, for example, N,N'-dialkyl-para-phenylenediamines, it being possible for the alkyl radicals to be identical or different, hydroxylamines, such as, for example, N,N-diethylhydroxylamine, phosphorus-containing compounds, such as, for example, triphenylphosphine, triphenyl phosphite or triethyl phosphite, or sulfur-containing compounds, such as, for example, sulfur dioxide, diphenyl sulfide, phenothiazine or 5-tert-butyl-4-hydroxy-2-methylphenyl sulfide, and Irganox© types, Cupferron types© and copper salts.

These compounds can be used individually or in mixtures. The amounts range from 10 ppm to 5% by weight, in general from 50 ppm to 3% by weight, based on the alcohol used. The reaction can be carried out in an inert gas atmosphere (such as, for example, nitrogen, argon, helium) or optionally with addition of air or oxygen-containing gas mixtures.

In the esterification the catalysts known according to the prior art can be used. Conventional esterification catalysts are sulfuric acid, sulfurous acid, disulfuric acid, polysulfuric acids, sulfur trioxide, methanesulfonic acid, benzenesulfonic acid, $C_1$-$C_{30}$-alkylbenzenesulfonic acid, naphthalenesulfonic acid, sulfuric acid monoesters of $C_1$-$C_{30}$-alcohols, such as dodecyl sulfate, phosphoric acid, phosphorous acid, hypophosphorous acid, polyphosphoric acid, phosphoric acid esters of $C_1$-$C_{30}$-alcohols, hydrochloric acid, perchloric acid, acidic ion exchangers, heteropoly acids, "solid super acids", and salts of these acids, Lewis acids, such as boron trichloride, aluminum sulfate and iron trichloride.

In the transesterification, all catalysts described in the prior art can be used, such as, for example, magnesium, aluminum or titanium alcoholates, such as tetramethyl, tetraethyl, tetraisopropyl, tetrapropyl, tetraisobutyl and tetrabutyl titanate, titanium phenolates, zirconium alcoholates or alcoholates having further functionalities in the ligands, metal chelate compounds of, for example, hafnium, titanium, zirconium or calcium, alkali metal and magnesium alcoholates, organic tin compounds, such as dibutyltin oxide and dibutyltin oxychloride, or calcium and lithium compounds, for example oxides, hydroxides, carbonates or halides, cyanates of alkali metals or alkaline earth metals or basic supported catalysts.

The catalyst is optionally used in amounts of, preferably, from 0.01 to 10, in particular from 0.05 to 5% by weight, based on the total reaction mixture.

The esterifications can be carried out at temperatures of from 40 to 180° C. The range from 80 to 140° C. is preferably employed. The esterification is preferably carried out using an excess of unsaturated carboxylic acid. A pressure range from 1 mbar to 10 bar is preferably employed.

The esterification can be carried out continuously or batchwise.

EXAMPLES

Example 1

1400 kg of a methylpolyethylene glycol having a molar mass of 1100, 175 kg of methacrylic acid, 9.7 kg of concentrated (97%) sulfuric acid, 510 g of phenothiazine and 158 g of 2-methyloxazoline were initially introduced into an enameled reactor having a volume of 2.2 $m^3$. Heating was carried out for 8 hours at 125° C. while passing through nitrogen. Thereafter, the pressure was slowly decreased to 50 mbar in the course of 8 hours and kept there for 14 hours. A mixture of methacrylic acid and water was taken off as distillate. A conversion of 97% was determined by means of NMR. After emptying, no deposits or soiling by polymers were detectable in the vessel and in the plant parts for the distillation.

Example 2

1166 kg of an ethoxylate started with lauryl alcohol and having an average of 7 units of ethylene oxide, 319 kg of methacrylic acid, 11.7 kg of concentrated (97%) sulfuric acid, 3.2 kg of hypophosphorous acid, 920 g of phenothiazine, 280 g of para-methoxyphenol and 233 g of 2-methyloxazoline were initially introduced into an enameled reactor having a volume of 2.2 $m^3$. Heating was carried out for 3 hours at 125° C. while passing through nitrogen. Thereafter, the pressure was slowly decreased to 50 mbar in the course of 8 hours and kept there for 3 hours. A mixture of methacrylic acid and water was taken off as distillate. A conversion of 99% was determined by means of NMR. After emptying, no deposits or soiling by polymers were detectable in the vessel and in the plant parts for the distillation.

Example 3

990 kg of behenyl alcohol, 543 kg of xylene, 266 kg of acrylic acid, 16.5 kg of para-toluenesulfonic acid, 2.3 kg of para-methoxyphenol and 247 g of 2-methyloxazoline were initially introduced into an enameled reactor having a volume of 2.2 $m^3$. Heating to 130° C. was now effected and the temperature was increased to 170° C. in the course of 6 hours. The resulting water of reaction was distilled of as an azeotropic mixture, and the xylene was recycled into the reaction. After separation of water was no longer detectable, a conversion of 98% was determined by means of NMR. After emptying, no deposits or soiling by polymers were detectable in the vessel, the column and the separator.

Example 4

1300 kg of a polyethylene glycol having an average molar mass of 600, 259 kg of methacrylic acid, 11.5 kg of concentrated (97%) sulfuric acid, 1044 g of phenothiazine, 396 g of Ional K 65© and 466 g of 2-methyloxazoline were initially introduced into an enameled reactor having a volume of 2.2 $m^3$. Heating was carried out at 125° C. for 4 hours at 500 mbar while passing through nitrogen. Thereafter, the pressure was slowly decreased to 50 mbar in the course of 4 hours and kept there for 4 hours. A mixture of methacrylic acid and water was taken off as distillate. A conversion of 98% was determined by means of NMR. After emptying, no deposits or soiling by polymers were detectable in the vessel and in the plant parts for the distillation.

Example 5

1400 kg of a methyl polyethylene glycol having an average molar mass of 750, 259 kg of methacrylic acid, 9.5 kg of concentrated (97%) sulfuric acid, 746 g of phenothiazine, 280 g of Ional K 65© and 233 g of 2-methyloxazoline were initially introduced into an enameled reactor having a volume of 2.2 $m^3$. Heating was carried out at 125° C. for 2 hours at 500 mbar while passing through nitrogen. Thereafter, the pressure was slowly decreased to 50 mbar in the course of 10 hours and kept there for 4 hours. A mixture of methacrylic acid and water was taken off as distillate. A conversion of 96% was determined by means of NMR. After emptying, no deposits or soiling by polymers were detectable in the vessel and in the plant parts for the distillation.

Example 6

Comparative Example Without Oxazoline 1400 kg of a methyl polyethylene glycol having an average molar mass of 750, 259 kg of methacrylic acid, 9.5 kg of concentrated (97%) sulfuric acid, 746 g of phenothiazine and 280 g of Ional K 65® were initially introduced into an enameled reactor having a volume of 2.2 $m^3$. Heating was carried out at 125° C. for 2 hours at 500 mbar while passing through nitrogen. Thereafter, the pressure was slowly decreased to 50 mbar in the course of 10 hours and kept there for 4 hours. A mixture of methacrylic acid and water was taken off as distillate. A conversion of 96% was determined by means of NMR. After emptying, deposits and soiling by polymers were to be found in the vessel. Polymers had also formed in the plant areas in which the distillate condensed.

Example 7

1189 kg of an ethoxylate started with lauryl alcohol and having on average 7 units of ethylene oxide, 497 kg of methyl methacrylate, 25.9 kg of titanium tetraisopropylate, 770 g of butyl hydroxytoluene, 442 g of para-methoxyphenol and 178 g of 2-methyloxazoline were initially introduced into a reactor having a volume of 2.1 $m^3$. While passing through nitrogen, heating to 105° C. was effected and the distilling off of the methanol formed, together with excess methyl methacrylate, was begun. Thereafter, the temperature was slowly increased to 150° C. in the course of 7 hours and kept there for 2 hours. Finally, the temperature was decreased to 130° C. and the excess methyl methacrylate was distilled off at a pressure of 5 mbar. A conversion of 99% was determined by means of NMR. After emptying, no deposits or soiling by polymers were detectable in the vessel and in the plant parts for the distillation.

Example 8

1109 kg of N,N-didecylaminoethanol, 586 kg of methyl methacrylate, 3.2 kg of lithium hydroxide, 1.9 kg of phenothiazine and 320 g of 2-methyloxazoline were initially introduced into a reactor having a volume of 2.1 m³. While passing through nitrogen, heating was effected for 8 hours at 105° C. and the methanol formed was distilled off together with excess methyl methacrylate. Thereafter, the pressure was slowly decreased to 300 mbar in the course of 6 hours and kept there for 2 hours. A conversion of 96% was determined by means of NMR. After emptying, no deposits or soiling by polymers were detectable in the vessel and in the plant parts for the distillation.

Example 9

1385 kg of an ethoxylate started with tallow fatty alcohol and having on average 25 units of ethylene oxide, 305 kg of methyl methacrylate, 10.2 kg of titanium tetraisopropylate, 1.17 kg of butylhydroxyanisole, 850 g of N,N-diethylhydroxylamine and 277 g of 2-methyloxazoline were initially introduced into a reactor having a volume of 2.1 m³. While passing through nitrogen, heating to 120° C. was effected and distilling off of the methanol formed, together with excess methyl methacrylate, was begun. Thereafter, the temperature was slowly increased to 150° C. in the course of 9 hours and kept there for 2 hours. A conversion of 94% was determined by means of NMR. After emptying, no deposits or soiling by polymers were detectable in the vessel and in the plant parts for the distillation.

The invention claimed is:

1. A method for the preparation of esters from a reaction mixture of an alcohol and an olefinically unsaturated carboxylic acid or reactive derivative thereof, said method comprising reacting the alcohol with the olefinically unsaturated carboxylic acid or reactive derivative thereof, in the presence of from 1 ppm to 1% by weight, based on the weight of the reaction mixture, of at least one oxazoline of the formula 1

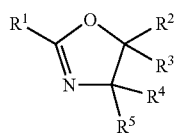

(1)

in which $R^1$, $R^2$, $R^3$, $R^4$ and $R^5$, independently of one another, are hydrogen or hydrocarbon radicals having from 1 to 12 carbon atoms, and $R^1$, $R^2$, $R^3$, $R^4$ and $R^5$ may be identical or different, being present.

2. The method as claimed in claim 1, wherein $R^1$, $R^2$, $R^3$, $R^4$ and $R^5$, independently of one another, are hydrogen or methyl groups.

3. The method as claimed in claim 1, wherein
   $R^1$ is methyl
   $R^2$ and $R^3$ are hydrogen
   $R^3$ and $R^5$ are hydrogen or methyl.

4. The method of claim 1, wherein the at least one oxazoline of formula 1 is present in amounts of from 10 ppm to 0.5% by weight based on the reaction mixture.

5. A method for stabilizing a reaction between an alcohol and an olefinically unsaturated carboxylic acid or reactive derivative thereof in a reaction mixture in the presence of a catalyst, said method comprising carrying out said reaction in the presence of a compound of formula 1

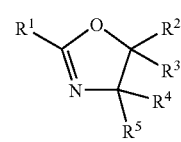

(1)

in which $R^1$, $R^2$, $R^3$, $R^4$ and $R^5$, in which $R^1$, $R^2$, $R^3$, $R^4$ and $R^5$, independently of one another, are hydrogen or hydrocarbon radicals having from 1 to 12 carbon atoms, and $R^1$, $R^2$, $R^3$, $R^4$ and $R^5$ may be identical or different, wherein said compound of formula (1) is present in an amount of from 1 ppm to 1% by weight, based on the weight of the reaction mixture.

6. A composition comprising
   A) an alcohol
   B) an olefinically unsaturated carboxylic acid or a reactive derivative thereof, the molar ratio A):B) being from 1:0.2 to 1:15,
   and
   C) 1 ppm to 1% by weight, based on the total weight of A) and B), of a compound of the formula 1

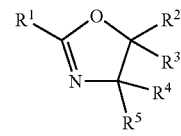

(1)

in which $R^1$, $R^2$, $R^3$, $R^4$ and $R^5$, independently of one another, are hydrogen or hydrocarbon radicals having from 1 to 12 carbon atoms, and $R^1$, $R^2$, $R^3$, $R^4$ and $R^5$ may be identical or different.

* * * * *